United States Patent
Myers et al.

(10) Patent No.: US 10,744,079 B2
(45) Date of Patent: Aug. 18, 2020

(54) ORAL CARE COMPOSITIONS AND USES THEREOF

(71) Applicants: Colgate-Palmolive Company, New York, NY (US); Rutgers, the State University of New Jersey, New Brunswick, NJ (US)

(72) Inventors: Carl Myers, Wayne, NJ (US); Guillaume Picquet, Long Valley, NJ (US); Kathryn E. Uhrich, Riverside, CA (US); Jennifer Chan Woo, Sandy, UT (US); Jeannette Elizabeth Marine, Sayreville, NJ (US)

(73) Assignees: Colgate-Palmolive Company, New York, NY (US); Rutgers, the State University of New Jersey, New Brunswick, NJ (US)

( * ) Notice: Subject to any disclaimer, the term of this patent is extended or adjusted under 35 U.S.C. 154(b) by 41 days.

(21) Appl. No.: 16/108,141

(22) Filed: Aug. 22, 2018

(65) Prior Publication Data
US 2019/0060210 A1 Feb. 28, 2019

Related U.S. Application Data

(60) Provisional application No. 62/549,085, filed on Aug. 23, 2017.

(51) Int. Cl.
*A61K 8/86* (2006.01)
*A61Q 11/00* (2006.01)
*A61K 8/55* (2006.01)

(52) U.S. Cl.
CPC .............. *A61K 8/86* (2013.01); *A61K 8/556* (2013.01); *A61Q 11/00* (2013.01)

(58) Field of Classification Search
None
See application file for complete search history.

(56) References Cited

U.S. PATENT DOCUMENTS

| 7,470,802 B2 | 12/2008 | Uhrich et al. |
| 8,192,754 B2 | 6/2012 | Uhrich et al. |
| 9,434,681 B2 | 9/2016 | Uhrich et al. |
| 9,630,905 B2 | 4/2017 | Uhrich et al. |
| 10,016,517 B2 | 7/2018 | York et al. |
| 2011/0229416 A1 | 9/2011 | Schrender |

FOREIGN PATENT DOCUMENTS

| WO | 2003/103594 | 12/2003 |
| WO | 2015/157241 | 10/2015 |

OTHER PUBLICATIONS

Djordjevic et al., 2005, "Polymeric Micelles Based on Amphiphilic Scorpion-like Macromolecules: Novel Carriers for Water-Insoluble Drugs," Pharmaceutical Research 22(1):24-32.
International Search Report and Written Opinion of the International Searching Authority in International Application No. PCT/US2018/047406 dated Nov. 12, 2018.

*Primary Examiner* — Brian J Davis

(57) ABSTRACT

Described herein are oral care compositions comprising amphiphilic macromolecules, along with methods of making and using same.

13 Claims, No Drawings

ORAL CARE COMPOSITIONS AND USES THEREOF

CROSS-REFERENCE TO RELATED APPLICATION

This application claims the benefit of priority from U.S. Provisional Application No. 62/549,085, entitled: "Oral Care Compositions and Uses Thereof", the contents of which are hereby incorporated by reference herein, in their entirety.

BACKGROUND

Bacteria attached to an oral surface can cause local and systemic pathology. For example, periodontitis and caries are caused by oral surface bacterial biofilm formation, and are among the most common oral diseases worldwide. Seeding of oral cavity bacteria into the bloodstream can occur during dental procedures and result in serious infections such as endocarditis and prosthetic joint infection.

A need exists for oral care products having an improved anti-bacterial effect to prevent and/or decrease the incidence of local and systemic pathology arising from bacterial attachment to an oral surface. The compositions and methods of the present invention address this need.

BRIEF SUMMARY

In some embodiments, the present invention provides a composition comprising an amphiphilic macromolecule (AM). In some embodiments, the AMs of the present invention are effective in (1) preventing or decreasing oral surface bacterial attachment, (2) stabilizing flavor in an oral care composition, or (3) both preventing or decreasing oral surface bacterial attachment and stabilizing flavor in an oral care composition.

In some embodiments, the present invention provides an oral care composition comprising any one of the compounds described herein.

DETAILED DESCRIPTION

Some embodiments of the present invention provide a composition comprising a compound having the structure of Formula (I):

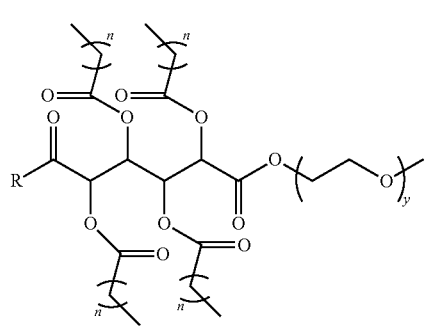

Formula (I)

wherein:
R is $NH(CH_2)_m PO_4$, wherein m is an integer from 1 to 6;
each n is independently selected from an integer between 2 and 20; and
y is an integer from 100 to 120; and
an orally acceptable carrier.

In some embodiments, the compound having a structure of Formula (I), has the structure of Compound A:

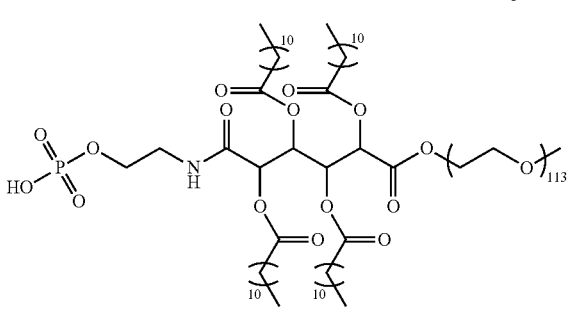

Compound A

In some embodiments, the compound having a structure of Formula (I), has the structure of Compound B:

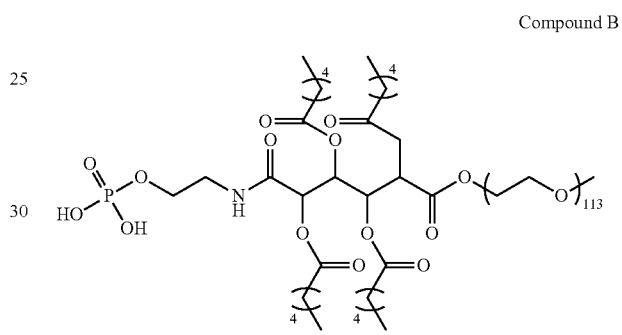

Compound B

Other embodiments provide a composition comprising a compound having a structure of Formula (II):

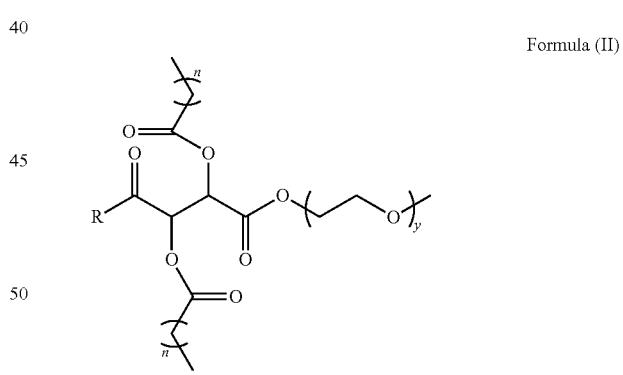

Formula (II)

wherein:
R is $NH(CH_2)_m PO_4$, wherein m is an integer from 1 to 6;
each n is independently from an integer between 2 and 20; and
y is an integer from 100 to 120; and
an orally acceptable carrier.

In some embodiments, m is 1, 2, 3, 4, 5 or 6. In some embodiments, m is 2.

In some embodiments, each n is independently selected from an integer between 3 and 19. In further embodiments, each n is independently selected from an integer between 4 and 18. In other embodiments, each n is independently selected from an integer between 4 and 15. In some embodiments, each n is independently selected from an integer between 4 and 12. Other embodiments provide a compound wherein each n is independently selected from an integer between 4 and 10. In some embodiments, each n is 4. In some embodiments, each n is 10. In other embodiments, each n is independently 2, 3, 4, 5, 6, 7, 8, 9, 10, 11, 12, 13, 14, 15, 16, 17, 18, 19 or 20.

In some embodiments, y is 100, 101, 102, 103, 104, 105, 106, 107, 108, 109, 110, 111, 112, 113, 114, 115, 116, 117, 118, 119 or 120. In some embodiments, y is an integer from 105 to 118. In some embodiments, y is an integer from 108 to 117. In some embodiments, y is an integer from 110 to 115. In some embodiments, y is 113.

Still further embodiments provide a composition comprising a compound of Formula (II), wherein the compound has the structure of Compound C:

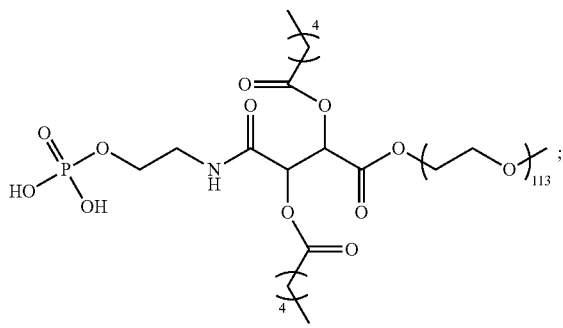

Compound C and
an orally acceptable carrier.

While other embodiments provide a composition comprising a compound of Formula (II), wherein the compound has the structure of Compound D:

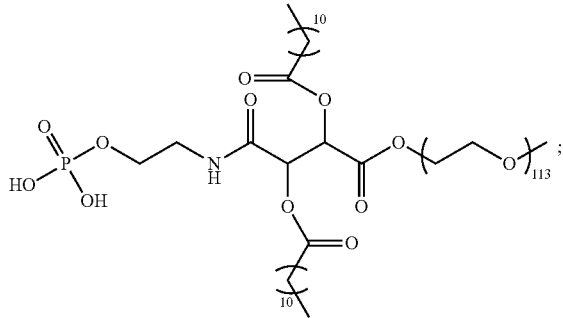

Compound D and
an orally acceptable carrier.

In some embodiments, the present invention provides a composition comprising any one of the compounds described herein. In some embodiments, the compositions are oral care compositions. In some embodiments, the oral care compositions comprise an orally acceptable carrier.

As used herein, the terms "oral composition(s)" or "oral care composition(s)" refer to a composition that is delivered to one or more surfaces of the oral cavity. Generally, during the normal course of use, the composition is not swallowed; rather, it is retained in the oral cavity for a time sufficient to contact one or more surfaces of the oral cavity and provide the desired benefit. Examples of such compositions include, but are not limited to, toothpaste, mouthwash or mouth rinse, oral gel, denture cleanser, and the like.

As used herein, the term "mouthrinse" or "mouthwash" refers to oral care compositions that are substantially liquid in character. In such a preparation the orally acceptable carrier typically has an aqueous phase comprising water or a water and alcohol mixture. Further, in various embodiments, the oral carrier includes a humectant and surfactant as described below. In various embodiments, the alcohol is typically ethyl alcohol.

In some embodiments, the oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., each of which are incorporated herein by reference. Representative fluoride ion sources used with the present invention include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. Where the formulation comprises calcium salts, the fluoride salts are preferably salts wherein the fluoride is covalently bound to another atom, e.g., as in sodium monofluorophosphate, rather than merely ionically bound, e.g., as in sodium fluoride.

In other embodiments, the compositions of the present invention may contain anionic surfactants, for example, water-soluble salts of higher fatty acid monoglyceride monosulfates, such as the sodium salt of the monosulfated monoglyceride of hydrogenated coconut oil fatty acids such as sodium N-methyl N-cocoyl taurate, sodium coco-glyceride sulfate; higher alkyl sulfates, such as sodium lauryl sulfate; higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or, for example sodium laureth-2 sulfate $(CH_3(CH_2)_{10}CH_2(OCH_2CH_2)_2OSO_3Na)$; higher alkyl aryl sulfonates such as sodium dodecyl benzene sulfonate (sodium lauryl benzene sulfonate); higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate. By "higher alkyl" is meant, e.g., $C_{6-30}$ alkyl. In particular embodiments, the anionic surfactant (where present) is selected from sodium lauryl sulfate and sodium ether lauryl sulfate. When present, the anionic surfactant is present in an amount which is effective, e.g., >0.001% by weight of the formulation, but not at a concentration which would be irritating to the oral tissue, e.g., 1%, and optimal concentrations depend on the particular formulation and the particular surfactant. In one embodiment, the anionic surfactant is present at from 0.03% to 5% by weight, e.g., 1.5%.

Cationic surfactants may also be included in compositions of the present invention, and can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants that can be used in some embodiments of the present invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In a particular embodiment, the composition of the invention comprises a nonionic surfactant selected from polaxamers (e.g., polaxamer 407), polysorbates (e.g., polysorbate 20), polyoxyl hydrogenated castor oils (e.g., polyoxyl 40 hydrogenated castor oil), and mixtures thereof.

Illustrative amphoteric surfactants that can be used in the compositions of the invention include betaines (such as cocamidopropyl betaine), derivatives of aliphatic secondary and tertiary amines in which the aliphatic radical can be a straight or branched chain and wherein one of the aliphatic substituents contains about 8-18 carbon atoms and one contains an anionic water-solubilizing group (such as carboxylate, sulfonate, sulfate, phosphate or phosphonate), and mixtures of such materials.

Illustrative zwitterionic surfactants that can be used in some embodiments of the present invention include derivatives of aliphatic quaternary ammonium, phosphonium and sulfonium compounds in which the aliphatic radical can be a straight or branched chain and wherein one of the aliphatic substituents contains about 8-18 carbon atoms and one contains an anionic water-solubilizing group (such as carboxy, sulfonate, sulfate, phosphate or phosphonate). The surfactant or mixtures of compatible surfactants can be present in the compositions of the present invention in 0.1% to 5%, in another embodiment 0.3% to 3% and in another embodiment 0.5% to 2% by weight of the total composition.

The oral care compositions of the invention may also include a flavoring agent. Flavoring agents which are used in the practice of the present invention include, but are not limited to, essential oils and various flavoring aldehydes, esters, alcohols, and similar materials, as well as sweeteners such as sodium saccharin. Examples of the essential oils include oils of spearmint, peppermint, wintergreen, *sassafras*, clove, sage, *eucalyptus*, marjoram, cinnamon, lemon, lime, grapefruit, and orange. Also useful are such chemicals as menthol, carvone, and anethole. Certain embodiments employ the oils of peppermint and spearmint. In some embodiments, the flavoring agent is incorporated in the oral composition at a concentration of 0.01 to 1% by weight.

In some embodiments, compounds of Formulas (I) and (II) help to solubilize the flavoring agent in the oral care composition.

The oral care compositions of the invention also may include one or more chelating agents able to complex calcium found in the cell walls of the bacteria. Binding of this calcium weakens the bacterial cell wall and augments bacterial lysis.

Another group of agents suitable for use as chelating or anti-calculus agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide least 0.1 wt. % pyrophosphate ions, e.g., 0.1 to 3 wt 5, e.g., 0.1 to 2 wt %, e.g., 0.1 to 1 wt %, e.g., 0.2 to 0.5 wt %. The pyrophosphates also contribute to preservation of the compositions by lowering the effect of water activity.

The oral care compositions of the invention also optionally include one or more polymers, such as polyethylene glycols, polyvinyl methyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of about 30,000 to about 1,000,000. These copolymers are available for example as Gantrez AN 139 (M.W. 500,000), AN 1 19 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1 103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorosorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, xanthan gum, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

The pH of the compositions of the present invention is generally between about 4.5 and about 10. The pH can be controlled with acid (e.g., citric acid or benzoic acid) or base (e.g., sodium hydroxide) or buffered (with sodium citrate, benzoate, carbonate, or bicarbonate, disodium hydrogen phosphate, or sodium dihydrogen phosphate, for example).

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of 0.001 wt. % to 10 wt. %, for example 0.01 wt. % to 5 wt. % or 0.1 wt. % to 1 wt. %.

In some embodiments, the compositions of the present invention comprise a tartar control (anticalculus) agent. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

In further embodiments, the oral compositions of the present invention comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

In yet other embodiments, the oral compositions of the present invention comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), and mixtures thereof.

In some embodiments, the present invention provides a method of treating conditions associated with the presence of oral bacteria comprising providing an oral composition in accordance with any of the above-described embodiments, and applying the oral composition to the oral cavity of the mammalian subject. In some embodiments, the method comprises repeating the application of the composition multiple times until the desired anti-bacterial and/or anti-inflammatory effects are achieved in the subject.

Further embodiments provide the use a composition as described herein for inhibiting or preventing bacterial adhesion to an oral cavity surface of a mammal. While other embodiments provide the use of a composition as described herein for treating, preventing or inhibiting the incidence of, or ameliorating the symptoms associated with, a systemic infection in a mammal.

In some embodiments, the present invention provides a composition comprising any one of the compounds described herein. In other embodiments, the present invention provides a composition comprising a compound described in U.S. Pat. No. 7,470,802. In some embodiments, the compounds described herein (e.g. Compounds A to D) can be prepared in accordance with the methods described in US 2011/0229416.

Further embodiments of the present invention provide an oral care composition comprising a compound of Formula (III):

$$A\text{-}X\text{—}Y\text{—}Z\text{—}R_1 \tag{III}$$

wherein: A is a carboxy group or is absent; X is a straight chain or branched chain aliphatic group containing 2 carbons to about 20 carbons wherein the aliphatic group is substituted with 2 to about 20 hydroxy groups; Y is —C(═O)—, —C(═S)—, or is absent; Z is O, S or NH; and $R_1$ is a polyether, wherein one or more hydroxy groups of X are acylated with a fatty acid residue; and an orally acceptable carrier.

As used herein, the term polyether includes poly(alkylene oxides) having between about 2 and about 150 repeating units. Typically, the poly(alkylene oxides) have between about 50 and about 110 repeating units. The alkylene oxide units contain from 2 to 10 carbon atoms and may be straight chained or branched. Preferably, the alkylene oxide units contain from 2 to 10 carbon atoms. Poly(ethylene glycol) (PEG) is preferred. Alkoxy-, amino-, carboxy-, and sulfo-terminated poly(alkylene oxides) are preferred, with methoxy-terminated poly(alkylene oxides) being more preferred.

A preferred polyether has the following structure:

$R_5$—($R_6$—O—)$_a$—$R_6$-Q- wherein $R_5$ is a 1 to 20 carbon straight-chain or branched alkyl group, —OH, —OH$_7$, —NH$_2$, NHR$_7$, —NHR$_7$R$_8$, —CO$_2$H, —SO$_3$H (sulfo), —CH$_2$—OH, —CH$_2$—OR$_7$, —CH$_2$—O—CH$_2$—R$_7$, —CH$_2$—NH$_2$, —CH$_2$—NHR$_7$, —CH$_2$—NR$_7$R$_8$, —CH$_2$CO$_2$H, —CH$_2$SO$_3$H, or —O—C(=O)—CH$_2$—CH$_2$—C(=O)—O—;

$R_6$ is a 1 to 10 carbon straight-chain or branched divalent alkylene group;

each $R_7$ and $R_8$ is independently a 1 to 6 carbon straight-chain or branched alkylene group;

Q is —O—, —S—, or —NR$_7$; and a is an integer from 2 to 150, inclusive.

Another preferred polyether is methoxy terminated polyethylene glycol.

In a compound of Formula (III), a poly(alkylene oxide) can be linked to the polyol, for example, through an ether, thioether, amine, ester, thioester, thioamide, or amide linkage. Preferably, a poly(alkylene oxide) is linked to the polyol by an ester or amide linkage in a compound of Formula (III).

As used herein, the term fatty acid includes fatty acids and fatty oils as conventionally defined, for example, long-chain aliphatic acids that are found in natural fats and oils. Fatty acids typically comprise from about 2 to about 24 carbon atoms. Preferably, fatty acids comprise from about 6 to about 18 carbon atoms. The term "fatty acid" encompasses compounds possessing a straight or branched aliphatic chain and an acid group, such as a carboxylate, sulfonate, phosphate, phosphonate, and the like. The "fatty acid" compounds are capable of "esterifying" or forming a similar chemical linkage with hydroxy groups on the polyol. Examples of suitable fatty acids include caprylic, capric, lauric, myristic, myristoleic, palmitic, palmitoleic, stearic, oleic, linoleic, eleostearic, arachidic, behenic, erucic, and like acids. Fatty acids can be derived from suitable naturally occurring or synthetic fatty acids or oils, can be saturated or unsaturated, and can optionally include positional or geometric isomers. Many fatty acids or oils are commercially available or can be readily prepared or isolated using procedures known to those skilled in the art.

Exemplary embodiments of the present disclosure will be illustrated by reference to the following examples, which are included to exemplify, but not to limit the scope of the present invention.

EXAMPLES

Example 1

Compound A was prepared as follows. CDI (82.0 mg, 0.51 mmol) was added to a solution containing Compound E (1.50 g, 0.25 mmol) in anhydrous DMF (10.5 mL).

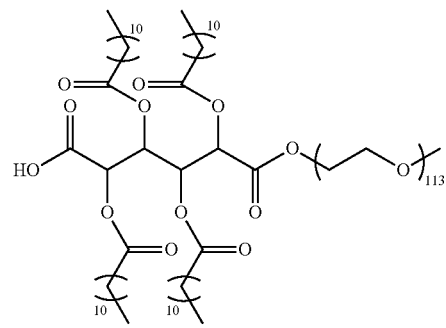

Compound E

The reaction mixture was stirred for 1.5 h at room temperature under a $N_2$ atmosphere and added to a solution of 2-aminoethyl dihydrogen phosphate (47.5 mg, 0.34 mmol) in water (10.5 mL) containing Et$_3$N (35 and the mixture was stirred at room temperature for 20 h. The reaction mixture was concentrated in vacuo. The resulting solids were dissolved in DCM and washed once with 0.1 M HCl (aq). The organic layer was washed once with saturated NaCl (aq) solution and dried over anhydrous MgSO$_4$. The solids were removed by filtration and the solvent was removed from the filtrate in vacuo. The resulting crude oil was dissolved in DCM and precipitated into cold Et$_2$O. Compound A was isolated via centrifugation at 3500 rpm for 5 min and decanting the supernatant. The pellet was washed with Et$_2$O (50 mL×3) and isolated via centrifugation.

A similar method was used to prepare Compound B, using Compound F as the starting material.

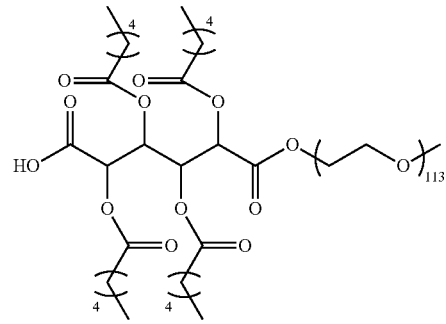

Compound F

Specifically, Compound F was activated with CDI followed by treatment with 2-aminoethylphosphate to afford Compound B. Compounds C and D can be prepared using similar methods, using Compounds G and H, respectively, as the starting materials.

Compound G

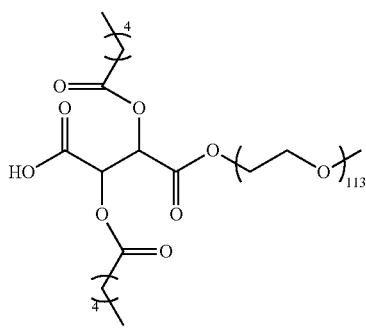

Compound H

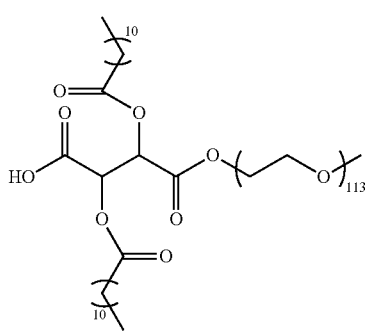

Compounds G and H can be prepared in accordance with the methods described in Tian, L., *Novel Amphiphilic Macromolecules for Drug Delivery Applications: Design, Synthesis and Characterization*. Rutgers University: 2004.

Compounds E and F can be prepared in accordance with the methods described in Tian et al., Amphiphilic Scorpion-like Macromolecules: Design, Synthesis, and Characterization. *Macromolecules* 2004, 37 (2), 538-543.

Example 2

Anti-Attachment Assay

Day 1: Over-Night Preparation: Fresh microbial cultures of *Actinomyces viscosus* (ATCC#43146) & *Streptococcus oralis* (ATCC#35037) were grown.

Day 2: Treatment:

An HAP coated MBEC Lid (Innovotech Catalog #19132) was placed into its corresponding 96-well plate containing simple solutions or formulations containing the amphiphilic macromolecules for 60 minutes at 37° C. After this time, the plate was rinsed to remove excess or loosely bound material by dipping the MBEC lid in ¼ concentrated TSB 10 times. The ¼ TSB was then changed and the rinsing procedure repeated for a total of three rinsing cycles. Equal volume over-night cultures of *A. viscosus* & *S. ° rails* were mixed together and the O.D. of the cultures was adjusted to 1.00 at 610 nm. To each of the 96 wells and 180 μl of bacteria solution was added, and the plate was incubated 3-4 hours at 37° C. Attached bacteria were removed by placing the MBEC lid into fresh ¼ TSB and sonicating for 2×2 minutes, rotating the plate 180° between sonication rounds. A representative sample of 100 μL was removed from each well and transferred to a black, clear-bottom plate (Corning Ref#3904). Bacteria count is measured by ATP bioluminescence using BacTiter-Glo Microbial Cell Viability Assay (Promega Ref# G8231) as per the manufacturer's instructions.

Table 1 (below) describes the results of the above-described experiment.

TABLE 1

| Compound | % Reduction |
|---|---|
| A | 65.0 |
| B | 46.2 |
| C | 42.3 |
| D | 40.2 |
| E | 47.4 |
| F | 25.1 |

Generally, a correlation between % reduction of bacterial adhesion and how much material was retained after rinsing on HAP-coated surfaces was observed. This data is described in Table 2 (below).

TABLE 2

| Compound | % Retained* | % Retained** | % Reduction of Bacterial Adhesion |
|---|---|---|---|
| A | 74 | 100 | 51.0 |
| B | 0 | 14 | 26.2 |
| C | 0 | 69 | 17.6 |
| D | 0 | 0 | 14.3 |
| E | 0 | 60 | 75.9 |
| F | 0 | 0 | 77.9 |

*HAP-coated QCM-D chips
**HAP-coated QCM-D chips (w/ Phosphate buffer)

Example 3

Flavor Stabilization Assay

Peppermint flavor oil was dissolved in propylene glycol, a typical procedure in the production of commercial mouthwash formulations. Exemplary compositions of the present invention comprising compounds described herein at concentrations of 1 w/w % and 2 w/w %; 7 w/w % propylene glycol; and 0.12 w/w % peppermint flavor are evaluated for turbidity in order to determine which compound(s) exhibited the greatest ability to solubilize flavor. Table 3 (below) describes the results of these evaluations.

TABLE 3

| Compound | Concentration (w/w %) | Transmittance (normalized) |
|---|---|---|
| Water | N/A | 1 |
| Poloxomer 407 | 1 | 0.99 |
| F | 1 | 0 |
|  | 2 | 0 |
| D | 1 | 0.019 |
|  | 2 | 0 |
| E | 1 | 0.37 |
|  | 2 | 0.78 |
| A | 1 | 0.19 |
|  | 2 | 0.90 |

Example 4

Compound A and Compound E are complexed with flavor and their ability to provide anti-attachment benefits, with and without flavor, is evaluated. Table 4 (below) describes the results of these evaluations, which demonstrate that the presence of a hydrophobic ingredient (e.g. a flavor) does not meaningfully compromise the anti-attachment efficacy of exemplary compounds of the present invention.

13

TABLE 4

| Compound | % Reduction |
|---|---|
| A | 51.0 |
| A + Flavor | 48.5 |
| E | 75.9 |
| E + Flavor | 78.8 |

Example 5

Hydroxyapatite discs (12 mm) are soaked in clarified saliva at 37° C. for 1 hour. After this time, the discs are rinsed and treated with 1.5 mL of a 1 wt % solution containing the materials for 1 hour. The discs are rinsed 3 times and then set in 1.5 mL bacteria solution (50/50 *A. viscosus/S. oralis*, with an O.D.=2 @ 610 nm) for 3 hours. Discs are rinsed, and then stained with SYTO 9 dye (3.34 mM, Invitrogen LIVE/DEAD BacLIGHT™ Bacterial Viability Kit (L7012), with a concentration of 6 uL/mL. Discs are then rinsed twice with quarter strength TSB buffer for final imaging.

Example 6

Table 5 (below) describes the formula of an exemplary oral care composition of the present invention.

| Ingredient | Wt. % |
|---|---|
| Amphiphilic Macromolecule (e.g. Compounds A-H) | 0-2 |
| Antibacterial | 0.01-0.1 |
| Sodium saccharin | 0.005-0.2 |
| Sodium benzoate | 0.01-0.1 |
| Potassium sorbate | 0.01-1 |
| Glycerin | 0-15 |
| Sorbitol | 0-15 |
| Poloxamer 407 | 0-2 |
| Propylene Glycol | 0-7 |
| Flavor | 0.05-1 |
| Color | 0.0001-0.005 |
| Water | Q.S. |

Compositions of the present invention, including the exemplary composition described in Table 5 (above), can be prepared according to methods generally known to those skilled in the art.

As used throughout, ranges are used as shorthand for describing each and every value that is within the range. Any value within the range can be selected as the terminus of the range.

All references cited herein are hereby incorporated by reference in their entireties. In the event of a conflict in a definition in the present disclosure and that of a reference cited herein, the present disclosure shall control.

Unless otherwise specified, all percentages and amounts expressed herein and elsewhere in the specification should be understood to refer to percentages by weight. The amounts given are based on the active weight of the material.

While the present invention has been described with reference to embodiments, it will be understood by those skilled in the art that various modifications and variations may be made therein without departing from the scope of the present invention as defined by the appended claims.

14

We claim:

1. An oral care composition comprising a compound of Formula (I):

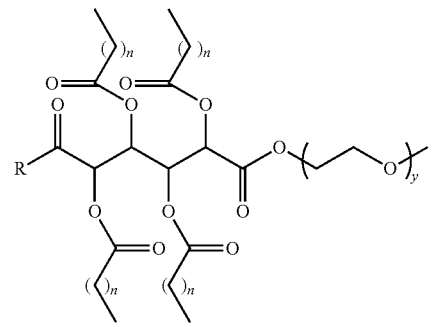

Formula (I)

wherein:

R is hydroxyl or —NH(CH$_2$)$_m$OP(O)(OH)$_2$, wherein m is an integer from 1 to 6;

each n is independently selected from an integer between 2 and 20; and y is an integer from 100 to 120; and an orally acceptable carrier.

2. The oral care composition according to claim 1, wherein each occurrence of n is an integer from 3 to 15.

3. The oral care composition according to claim 1, wherein y is an integer from 110 to 115.

4. The oral care composition according to claim 1, wherein the compound of Formula (I) has the structure of Compound A:

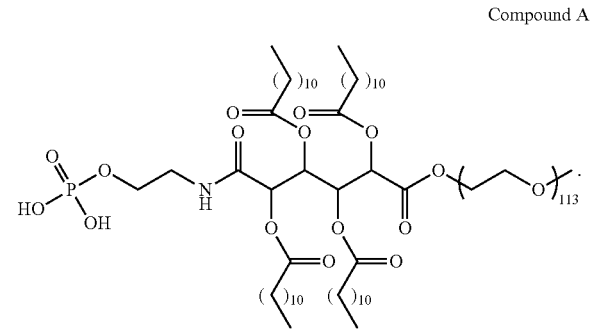

Compound A

5. The oral care composition according to claim 1, wherein the compound of Formula (I) has the structure of Compound B:

Compound B

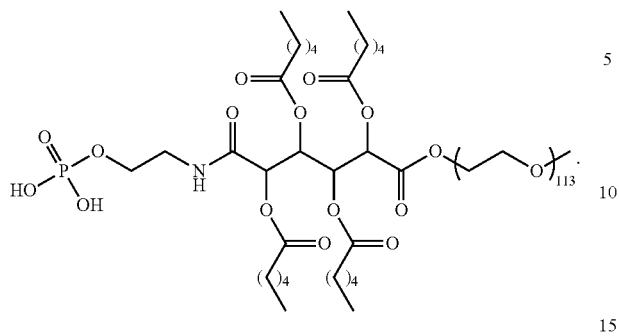

6. The oral care composition of claim 1, wherein the compound of Formula (I) has the structure of Compound E:

Compound E

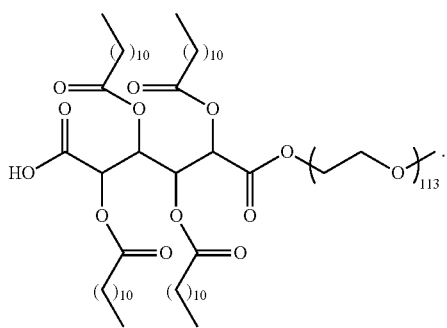

7. The oral care composition according to claim 1, wherein the compound of Formula (II) has the structure of Compound F:

Compound F

8. The oral care composition according to claim 1, wherein the oral care composition is in a form selected from a mouth rinse; a toothpaste; and an oral spray.

9. The oral care composition according to claim 1, further comprising a humectant, a flavoring, and/or a surfactant.

10. A method for inhibiting or preventing bacterial adhesion to an oral cavity surface comprising contacting an oral cavity surface of a mammal with an oral care composition according to claim 1.

11. A method for treating, preventing or inhibiting the incidence of, or ameliorating the symptoms associated with, a systemic infection, comprising: contacting an oral cavity surface of a mammal in need thereof with an oral care composition according to claim 1.

12. The oral care composition according to claim 2, wherein each occurrence of n is 4.

13. The oral care composition according to claim 2, wherein each occurrence of n is 10.

* * * * *